(12) United States Patent
Shintani (10) Patent No.: US 12,151,139 B2
(45) Date of Patent: Nov. 26, 2024

(54) WALKING TRAINING SYSTEM, CONTROL METHOD OF SAME, AND NON-TRANSITORY STORAGE MEDIUM

(71) Applicant: TOYOTA JIDOSHA KABUSHIKI KAISHA, Toyota (JP)

(72) Inventor: Kazuhiro Shintani, Toyokawa (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 266 days.

(21) Appl. No.: 17/729,213

(22) Filed: Apr. 26, 2022

(65) Prior Publication Data

US 2022/0395726 A1    Dec. 15, 2022

(30) Foreign Application Priority Data

Jun. 15, 2021    (JP) ................................. 2021-099387

(51) Int. Cl.
  *A63B 24/00*    (2006.01)
  *A61H 1/02*    (2006.01)
  (Continued)

(52) U.S. Cl.
  CPC .......... *A63B 24/0062* (2013.01); *A63B 22/02* (2013.01); *A61H 1/0262* (2013.01);
  (Continued)

(58) Field of Classification Search
  CPC . A63B 24/0062; A63B 22/02; A63B 71/0622; A63B 2022/0094; A63B 2220/05; A63B 2220/30; A63B 2220/50; A63B 2220/805; A63B 2220/807; A63B 2220/836; A63B 2230/62; A63B 21/285; A63B 71/0009; A63B 21/0058;
  (Continued)

(56) References Cited

U.S. PATENT DOCUMENTS 11,141,343 B2 * 10/2021 Sugata ............. A63B 21/00181
11,452,918 B2 *  9/2022 Shintani ............. A63B 24/0087
(Continued)

FOREIGN PATENT DOCUMENTS

JP    2015-107247 A    6/2015
JP    2015107247    * 11/2015    ............... A61H 1/02
(Continued)

*Primary Examiner* — Loan B Jimenez
*Assistant Examiner* — Andrew M Kobylarz
(74) *Attorney, Agent, or Firm* — Oliff PLC (57) ABSTRACT

A walking training system includes a treadmill, a center-of-gravity position detection unit that detects a center-of-gravity position of a trainee from a load received from a sole of the trainee on a belt of the treadmill, a posture detection unit that detects a posture of the trainee, a center-of-gravity position estimation unit that estimates the center-of-gravity position of the trainee from the detected posture of the trainee, a determination unit that determines whether a difference between the detected center-of-gravity position and the estimated center-of-gravity position exceeds a predetermined value, and a notification unit that sends, when the determination unit determines that the difference exceeds the predetermined value, a notification notifying that whether the difference exceeds the predetermined value.

4 Claims, 7 Drawing Sheets

(51) Int. Cl.
*A63B 22/00* (2006.01)
*A63B 22/02* (2006.01)
*A63B 71/06* (2006.01)

(52) U.S. Cl.
CPC ... *A63B 2022/0094* (2013.01); *A63B 71/0622* (2013.01); *A63B 2220/05* (2013.01); *A63B 2220/30* (2013.01); *A63B 2220/50* (2013.01); *A63B 2220/805* (2013.01); *A63B 2220/807* (2013.01); *A63B 2220/836* (2013.01); *A63B 2230/62* (2013.01)

(58) Field of Classification Search
CPC .............. A63B 21/153; A63B 69/0057; A63B 2071/0081; A63B 2071/0658; A63B 2220/16; A63B 2220/44; A63B 2220/51; A63B 2220/52; A63B 2225/50; A63B 21/00181; A63B 21/068; A63B 22/0242; A63B 26/003; A63B 69/0064; A63B 23/04; A63B 23/0494; A63B 24/0087; A61H 1/0262; A61B 5/4836; A61B 5/1038; A61B 5/1128; A61B 5/746; A61B 5/1121; A61B 5/1116; G06T 7/66; G06V 40/25

See application file for complete search history.

(56) References Cited

U.S. PATENT DOCUMENTS

| | | | |
|---|---|---|---|
| 2015/0294481 A1* | 10/2015 | Sakaue | G06V 40/23 600/595 |
| 2020/0289894 A1* | 9/2020 | Shintani | A63B 26/003 |
| 2021/0000677 A1* | 1/2021 | Otsuki | G06V 10/82 |
| 2022/0331664 A1* | 10/2022 | Nakamura | A61H 1/0262 |

FOREIGN PATENT DOCUMENTS

| | | |
|---|---|---|
| JP | 6187208 B2 | 8/2017 |
| JP | 2018-093966 A | 6/2018 |
| JP | 2020-146330 A | 9/2020 |
| JP | 2021-009565 A | 1/2021 |

* cited by examiner

CP: DETECTED CENTER OF GRAVITY (ACTUAL CENTER OF GRAVITY)
CPx: ESTIMATED CENTER OF GRAVITY

FIG. 6

CP: DETECTED CENTER OF GRAVITY (ACTUAL CENTER OF GRAVITY)
CPx: ESTIMATED CENTER OF GRAVITY

FIG. 7

WALKING TRAINING SYSTEM, CONTROL METHOD OF SAME, AND NON-TRANSITORY STORAGE MEDIUM

CROSS-REFERENCE TO RELATED APPLICATION

This application claims priority to Japanese Patent Application No. 2021-099387 filed on Jun. 15, 2021, incorporated herein by reference in its entirety.

BACKGROUND

1. Technical Field

The present disclosure relates to a walking training system, a control method thereof, and a non-transitory storage medium.

2. Description of Related Art

Japanese Patent No. 6187208 discloses a walking rehabilitation system which includes a treadmill, a floor reaction force sensor that measures a reaction force applied to the treadmill, a leg robot attached to a lower limb of a user, a distance image camera that captures a distance of the lower limb equipped with the leg robot, and a load estimator that estimates sole loads of right and left lower limbs of the user based on a measured value of the floor reaction force sensor and the image captured by the distance image camera.

SUMMARY

In the related technology, when support for a user (a trainee) by an assistant is excessive in a case where the user is executing walking training with the support of the assistant, the user might not perform effective walking training.

The present disclosure provides a walking training system, a control method of the walking training system, and a non-transitory storage medium that enable a trainee to perform effective walking training by sending a notification to an assistant who excessively supports the trainee of that effect.

A walking training system according to a first aspect of the present disclosure includes a treadmill, a center-of-gravity position detection unit configured to detect a center-of-gravity position of a trainee from a load received from a sole of the trainee on a belt of the treadmill, a posture detection unit configured to detect a posture of the trainee, a center-of-gravity position estimation unit configured to estimate the center-of-gravity position of the trainee from the detected posture of the trainee, a determination unit configured to determine whether a difference between the detected center-of-gravity position and the estimated center-of-gravity position exceeds a predetermined value, and a notification unit configured to, when the determination unit determines that the difference exceeds the predetermined value, send a notification notifying that the difference exceeds the predetermined value. When the difference (the deviation) between the actual center-of-gravity position of the trainee who is conducting walking training with the support of an assistant and the center-of-gravity position estimated from the posture of the trainee becomes larger than the predetermined value, the walking training system determines that the support for the trainee by the assistant is excessive and notifies the assistant of that effect. As a result, the assistant who received the notification can, for example, offer the trainee less support, and thus the trainee can perform effective walking training.

In the first aspect, the center-of-gravity position detection unit may be a load distribution sensor that is installed under the belt of the treadmill such that the load distribution sensor is not interlocked with the belt and is configured to detect a distribution of the load received from the sole of the trainee on the belt of the treadmill.

In the first aspect, the center-of-gravity position detection unit may include a pair of load sensors configured to be attached to respective soles of a right leg and a left leg of the trainee and a first image capturing unit configured to capture images of at least the right and left legs of the trainee, and detect the center-of-gravity position of the trainee based on loads detected by the load sensors and respective positions of the right and left legs of the trainee identified from the images captured by the first image capturing unit.

In the first aspect, the posture detection unit may include a second image capturing unit configured to capture an image of the trainee and a posture information extraction unit configured to extract information on the posture of the trainee from the image of the trainee captured by the second image capturing unit. The center-of-gravity position estimation unit may estimate the center-of-gravity position of the trainee from the posture of the trainee extracted by the posture information extraction unit.

In the first aspect, the posture detection unit may include an infrared sensor configured to detect the trainee and a posture information extraction unit configured to extract information on the posture of the trainee from a detection result of the trainee by the infrared sensor. The center-of-gravity position estimation unit may estimate the center-of-gravity position of the trainee from the posture of the trainee extracted by the posture information extraction unit.

In the first aspect, the predetermined value may be determined according to at least one of the walking speed of the trainee and a motion speed of a predetermined part of the trainee.

In the first aspect, the predetermined value may be set to a larger value as a walking speed of the trainee becomes faster, and may be set to a smaller value as the walking speed of the trainee becomes slower.

In the first aspect, the predetermined value may be determined such that the difference between the detected center-of-gravity position and the estimated center-of-gravity position is offset when an assistant does not support the trainee.

In the first aspect, when a predetermined abnormal movement is detected, the notification unit does not have to send the notification even when the difference between the detected center-of-gravity position and the estimated center-of-gravity position exceeds the predetermined value.

A control method of a walking training system according to a second aspect of the present disclosure includes detecting a center-of-gravity position of a trainee from a load received from a sole of the trainee on a belt of a treadmill by using a center-of-gravity position detection unit, detecting a posture of the trainee, estimating the center-of-gravity position of the trainee from the detected posture of the trainee by using a center-of-gravity position estimation unit, determining whether a difference between the detected center-of-gravity position and the estimated center-of-gravity position exceeds a predetermined value, and sending, when a determination is made that the difference exceeds the predetermined value, a notification notifying that the difference exceeds the predetermined value. When the difference (the deviation) between the actual center-of-gravity position of the trainee who is executing walking training with the support of an assistant and the center-of-gravity position estimated from the posture of the trainee becomes larger than the predetermined value, the control method of the walking training system determines that the support for the trainee by the assistant is excessive and notifies the assistant of that effect. As a result, the assistant who received the notification can, for example, offer the trainee less support, and thus the trainee can perform effective walking training.

A third aspect of the present disclosure is a non-transitory storage medium storing instructions that are executable by one or more processors and that cause the one or more processors to perform functions. The functions include detecting a center-of-gravity position of a trainee from a load received from a sole of the trainee on a belt of a treadmill by using a center-of-gravity position detection unit, detecting a posture of the trainee, estimating the center-of-gravity position of the trainee from the detected posture of the trainee by using a center-of-gravity position estimation unit, determining whether a difference between the detected center-of-gravity position and the estimated center-of-gravity position exceeds a predetermined value, and sending, when a determination is made that the difference exceeds the predetermined value, a notification notifying that the difference exceeds the predetermined value. According to the non-transitory storage medium, when the difference (the deviation) between the actual center-of-gravity position of the trainee who is executing walking training with the support of an assistant and the center-of-gravity position estimated from the posture of the trainee becomes larger than the predetermined value, it is determined that the support for the trainee by the assistant is excessive and the assistant is notified of that effect. As a result, the assistant who receives the notification can, for example, offer the trainee less support, and thus the trainee can perform effective walking training.

With each aspect of the present disclosure, it is possible to provide a walking training system, a control method of the walking training system, and a non-transitory storage medium that enable a trainee to perform effective walking training by sending a notification to an assistant who excessively supports the trainee of that effect.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Hereinafter, the present disclosure will be described through embodiments of the disclosure, but the disclosure according to the claims is not limited to the following embodiments. Moreover, not all of the configurations described in the embodiments are indispensable for solving the problem. In order to make the description clearer, the description and drawings hereinafter are omitted or simplified as appropriate. In each drawing, the same elements are denoted by the same reference signs, and duplicate descriptions are omitted as necessary.

First Embodiment

Figure 1:
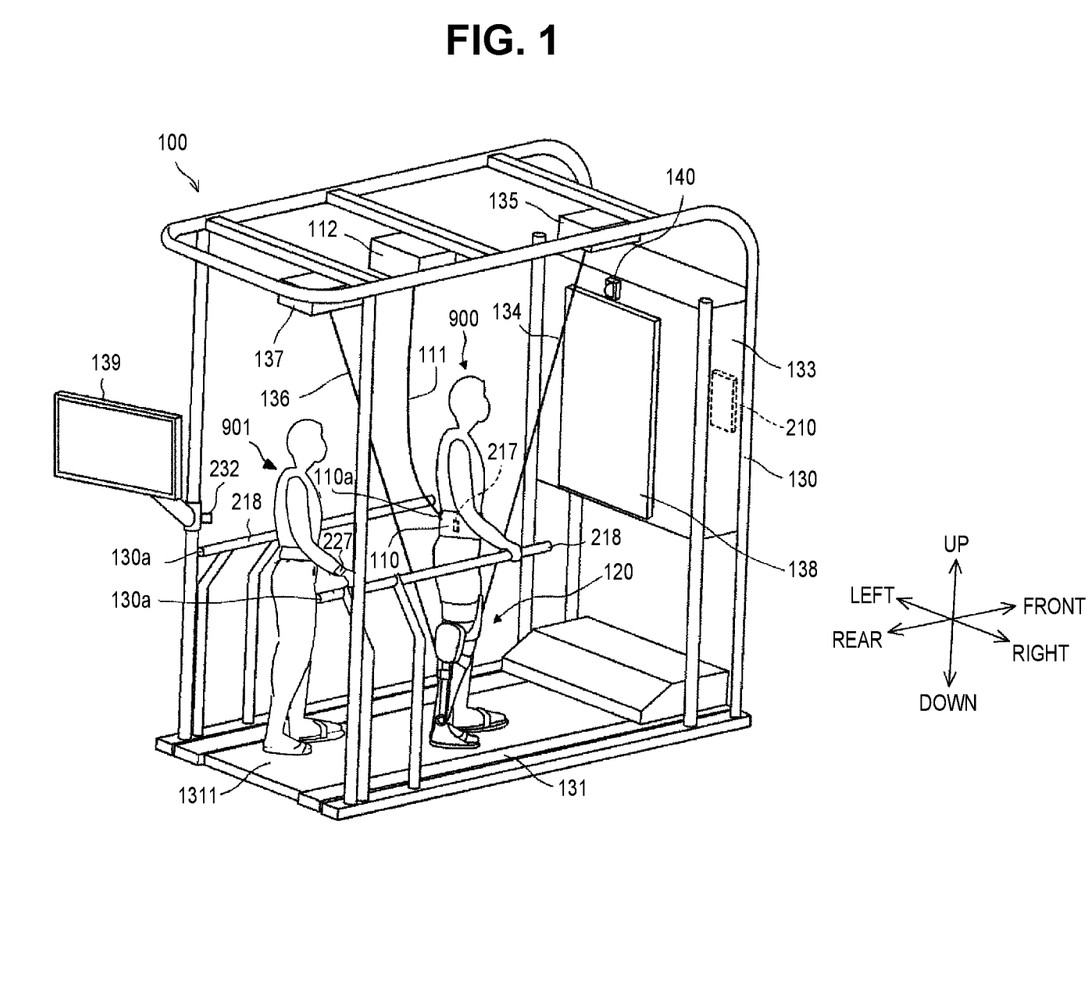
FIG. 1 is an overall conceptual view illustrating a configuration example of a walking training device according to a first embodiment.

FIG. 1 is an overall conceptual view illustrating a configuration example of a walking training device according to a first embodiment. A walking training device 100 according to the present embodiment is a specific example of a rehabilitation support device that supports the rehabilitation of a trainee (user) 900, and is particularly a specific example of a walking training device that supports walking training. The walking training device 100 is a device that enables the trainee 900, who is a hemiplegic patient suffering from paralysis in one leg, to perform walking training according to guidance of a training staff member 901. Here, the training staff member 901 can be, for example, a therapist (physiotherapist) or a doctor. In addition, since the training staff member 901 assists the training of the trainee by guidance, assistance, or the like, he or she can be referred to as a training instructor, a training assistant, a training helper, or the like. The walking training device 100 can also be called a walking training system. In the following description, a vertical direction, a lateral direction, and a longitudinal direction are directions relative to the direction of the trainee 900.

The walking training device 100 mainly includes a control panel 133 attached to a frame 130 forming a whole skeleton, a treadmill 131 on which the trainee 900 walks, and a walking assist device (a robot leg) 120 attached to an affected leg, which is the leg on the paralyzed side of the trainee 900.

The treadmill 131 is a device that encourages the trainee 900 to walk, and the trainee 900 who performs walking training steps on a belt 1311 and attempts a walking motion according to the movement of the belt 1311. The training staff member 901 can also stand on the belt 1311 behind the trainee 900 and perform a walking motion together, as illustrated in FIG. 1, for example. However, normally, it is preferable that the training staff member 901 be in a state where it is easy to assist the trainee 900, such as standing while straddling the belt 1311.

Figure 2:
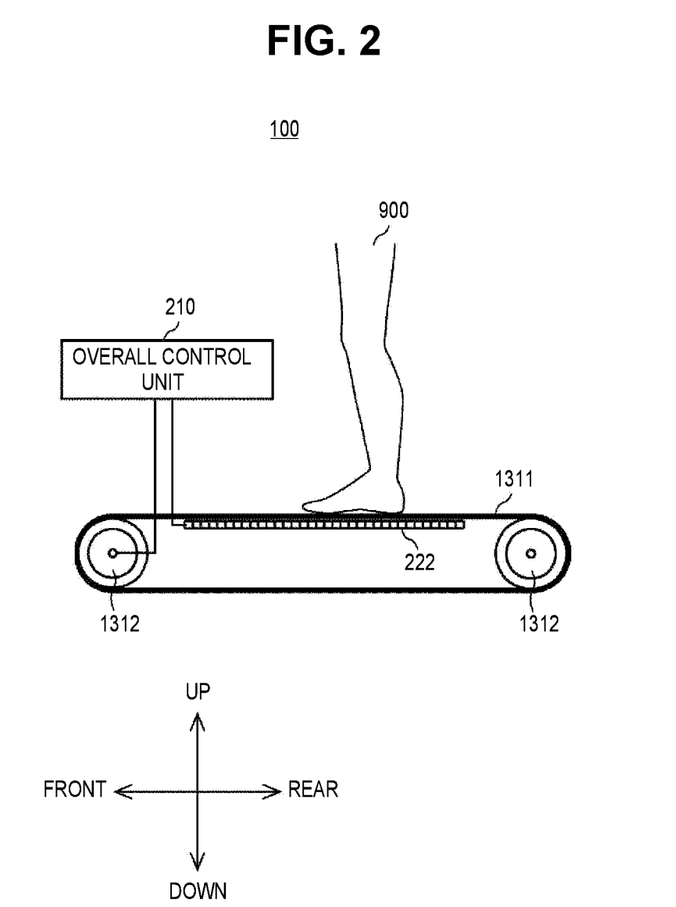
FIG. 2 is a schematic side view of a part of a treadmill provided in the walking training device illustrated in FIG. 1.

FIG. 2 is a schematic side view of a part of the treadmill 131. As illustrated in FIG. 2, the treadmill 131 includes at least the belt 1311 with a ring shape, a pulley 1312, and a motor (not shown). Further, a load distribution sensor 222 is installed radially inward of the belt 1311 (a lower side of a surface of the belt 1311, which is the surface on which the trainee 900 steps) so as not to be interlocked with the belt 1311. However, the load distribution sensor 222 may be provided on the upper side of the belt 1311 so as to be interlocked with the belt 1311. The load distribution sensor 222 is an example of a center-of-gravity position detection unit 225. Other examples of the center-of-gravity position detection unit 225 will be described below.

The load distribution sensor 222 is composed of a plurality of sensors, and the sensors are arranged in a matrix under the belt 1311 that supports the sole of the trainee 900. By using the sensors, the load distribution sensor 222 can detect the magnitude and distribution of a surface pressure (a load) received from the sole of the trainee 900. For example, the load distribution sensor 222 is a resistance-change-detection-type load detection sheet on which a plurality of electrodes is arranged in a matrix. From the detection result of the load distribution sensor 222, it is possible to determine the walking state (whether each leg is in a standing state or a swinging state, and the like) of the trainee 900. The details of a method of determining the walking state of the trainee 900 based on the detection result of the load distribution sensor 222 will be described below.

In the treadmill 131, for example, an overall control unit 210, which will be described below, determines the walking state of the trainee 900 based on the detection result of the load distribution sensor 222, and rotates the pulley 1312 using the motor (not shown) according to the walking state in such a manner that the belt 1311 with a ring shape rotates (moves). As a result, the trainee 900 can perform walking training without sticking out from the belt 1311.

The frame 130 is erected on the treadmill 131 installed on the floor. The frame 130 supports the control panel 133 that accommodates the overall control unit 210 that controls motors and sensors, and a training monitor 138 that may be, for example, a liquid crystal panel that presents the progress state of training to the trainee 900. Further, the frame 130 supports a front tension unit 135 near the front of the upper head of the trainee 900, a harness tension unit 112 near the upper head, and a rear tension unit 137 near the rear of the upper head. In addition, the frame 130 includes handrails 130a for the trainee 900 to grab.

The handrails 130a are arranged on both the right and left sides of the trainee 900. Each of the handrails 130a is arranged in a direction parallel to a walking direction of the trainee 900. A vertical position and a horizontal position of the handrail 130a can be adjusted. That is, the handrails 130a can include mechanisms for changing their height and width. Further, the handrail 130a can be configured such that an inclination angle thereof can be changed by adjusting the height such that the heights on, for example, the front side and on the rear side in the walking direction differ from each other. For example, the handrail 130a can have an inclination angle at which the height gradually increases along the walking direction.

Further, the handrail 130a is provided with a handrail sensor 218 used for detecting a load received from the trainee 900. For example, the handrail sensor 218 can be a resistance-change-detection-type load detection sheet on which the electrodes are arranged in a matrix. Further, the handrail sensor 218 can be a six-axis sensor in which a three-axis acceleration sensor (x, y, z) and a three-axis gyro sensor (roll, pitch, yaw) are combined. However, the type and an installation position of the handrail sensor 218 do not matter.

A camera 140 functions as an image capturing unit used for observing the whole body of the trainee 900. The camera 140 is installed in the vicinity of the training monitor 138 so as to face the trainee 900. The camera 140 captures still images and moving images of the trainee 900 who is training. The camera 140 includes a set of a lens and an image capturing element in which the angle of view is set so as to be able to capture an image of the whole body of the trainee 900. The image capturing element may be, for example, a complementary metal-oxide-semiconductor (CMOS) image sensor, and converts an optical image formed on an image plane into an image signal. Here, by using a posture detection unit 226 described below, it is possible to extract information on the posture of the trainee 900 from the whole body image of the trainee 900 captured by the camera 140.

By a coordinated operation of the front tension unit 135 and the rear tension unit 137, the load of the walking assist device 120 is offset such that the load does not become a burden on the affected leg, and further, the swinging motion of the affected leg is assisted according to the degree of setting.

A first end of a front wire 134 is connected to a winding mechanism of the front tension unit 135, and a second end thereof is connected to the walking assist device 120. The winding mechanism of the front tension unit 135 winds and unwinds the front wire 134 according to the movement of the affected leg by turning a motor on and off (not shown). Similarly, a first end of a rear wire 136 is connected to a winding mechanism of the rear tension unit 137, and a second end thereof is connected to the walking assist device 120. The winding mechanism of the rear tension unit 137 winds and unwinds the rear wire 136 according to the movement of the affected leg by turning a motor on and off (not shown). By the coordinated operation of the front tension unit 135 and the rear tension unit 137, the load of the walking assist device 120 is offset such that the load does not become a burden on the affected leg, and further, the swinging motion of the affected leg is assisted according to the degree of setting.

For example, as an operator, the training staff member 901 sets a high level of assistance for a trainee who is severely paralyzed. When the assist level is set to be high, the front tension unit 135 winds the front wire 134 with a relatively large force according to a swing time of the affected leg. As the training progresses and assistance is no longer needed, the training staff member 901 sets the assist level to the minimum. When the assist level is set to the minimum, the front tension unit 135 winds the front wire 134 with a force sufficient to cancel the weight of the walking assist device 120 according to the swing time of the affected leg.

The walking training device 100 further includes a fall prevention harness device composed of an orthotic device 110, a harness wire 111, and the harness tension unit 112.

The orthotic device 110 is a belt wrapped around the abdomen of the trainee 900 and is fixed to the abdomen by, for example, a hook-and-loop fastener. The orthotic device 110 includes a connecting hook 110a used for connecting a first end of the harness wire 111 which is a suspending tool, and can also be referred to as a hanger belt. The trainee 900 wears the orthotic device 110 such that the connecting hook 110a is located on the back.

The first end of the harness wire 111 is connected to the connecting hook 110a of the orthotic device 110, and a second end thereof is connected to a winding mechanism of the harness tension unit 112. The winding mechanism of the harness tension unit 112 winds and unwinds the harness wire 111 by turning a motor on and off (not shown). With such a configuration, when the trainee 900 is about to fall, the fall prevention harness device winds the harness wire 111 according to an instruction of the overall control unit 210 that detects the movement, and supports the upper body of the trainee 900 by the orthotic device 110 to prevent the trainee 900 from falling.

The orthotic device 110 includes a posture sensor 217 used for detecting the posture of the trainee 900. The posture sensor 217 may be, for example, a combination of a gyro sensor and an acceleration sensor, and outputs an inclination angle of the abdomen to which the orthotic device 110 is attached in a direction of gravity.

A management monitor 139 is a display input device mainly used for monitoring and operation by the training staff member 901, and is attached to the frame 130. The management monitor 139 may be, for example, a liquid crystal panel, and a touch panel is provided on the surface thereof. The management monitor 139 displays various menu items related to training settings, various parameter values at the time of training, training results, or the like. Further, an emergency stop button 232 is provided in the vicinity of the management monitor 139. When the training staff member 901 presses the emergency stop button 232, the walking training device 100 makes an emergency stop. Further, for example, a notification unit 227 is provided on the side of the training staff member 901.

The walking assist device 120 is attached to the affected leg of the trainee 900 and assists the walking of the trainee 900 by reducing the load of extension and flexion at the knee joint of the affected leg. The walking assist device 120 transmits data on the leg movement obtained by walking training to the overall control unit 210, and drives a joint portion according to an instruction from the overall control unit 210. The walking assist device 120 can also be connected to a hip joint (a connecting member having a rotating portion) attached to the orthotic device 110, which is a part of the fall prevention harness device, via a wire or the like.

Details of Walking Assist Device

Figure 3:
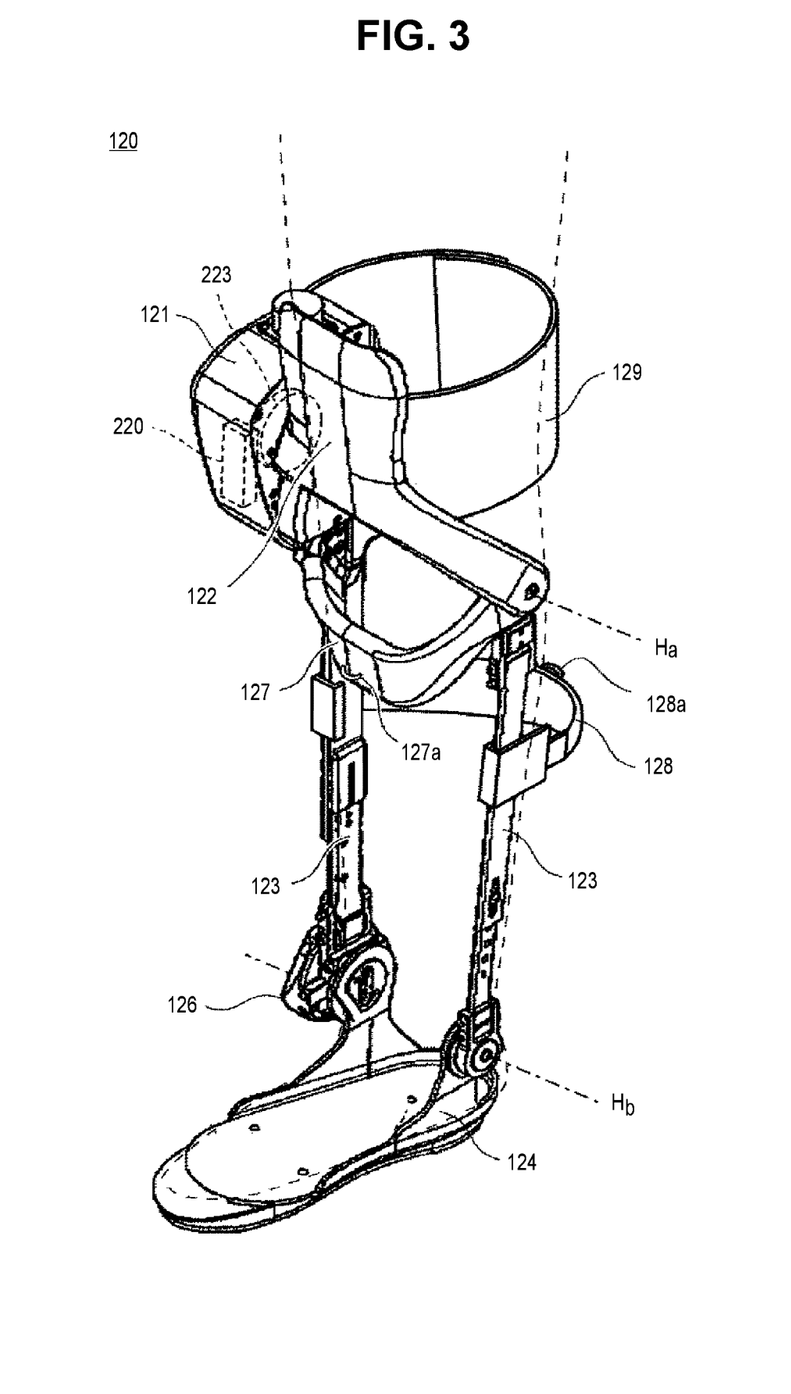
FIG. 3 is a schematic perspective view illustrating a configuration example of a walking assist device provided in the walking training device illustrated in FIG. 1.

FIG. 3 is a schematic perspective view illustrating a configuration example of the walking assist device 120. The walking assist device 120 mainly includes a control unit 121 and a plurality of frames that supports each part of the affected leg. The walking assist device 120 is also referred to as a robot leg.

The control unit 121 includes an auxiliary control unit 220 that controls the walking assist device 120, and also includes a motor (not shown) that generates a driving force for assisting the extension and flexion movements of the knee joint. The frames that support parts of the affected leg include an upper thigh frame 122, and a lower thigh frame 123 pivotably connected to the upper thigh frame 122. In addition, the frames include a foot flat frame 124 pivotably connected to the lower thigh frame 123, a front connecting frame 127 used for connecting the front wire 134, and a rear connecting frame 128 used for connecting the rear wire 136.

The upper thigh frame 122 and the lower thigh frame 123 pivot relative to each other around an illustrated hinge axis Ha. The motor of the control unit 121 rotates according to the instruction of the auxiliary control unit 220 to apply force to the upper thigh frame 122 and the lower thigh frame 123 to open or close relatively around the hinge axis Ha. An angle sensor 223 accommodated in the control unit 121 may be, for example, a rotary encoder, and detects the angle formed by the upper thigh frame 122 and the lower thigh frame 123 around the hinge axis Ha. The lower thigh frame 123 and the foot flat frame 124 pivot relative to each other around an illustrated hinge axis Hb. The angle range of relative pivoting is pre-adjusted by an adjusting mechanism 126.

The front connecting frame 127 is provided so as to extend on the front side of the upper thigh in the right-left direction and connect to the upper thigh frame 122 at both ends. Further, the front connecting frame 127 is provided with the connecting hook 127a used for connecting the front wire 134 near the center in the right-left direction. The rear connecting frame 128 is provided so as to extend on the rear side of the lower thigh in the right-left direction and connect to the lower thigh frames 123 which extend up and down at both ends, respectively. Further, the rear connecting frame 128 is provided with the connecting hook 128a used for connecting the rear wire 136 near the center in the right-left direction.

The upper thigh frame 122 includes an upper thigh belt 129. The upper thigh belt 129 is a belt integrally provided on the upper thigh frame, and is wrapped around the upper thigh of the affected leg to fix the upper thigh frame 122 to the upper thigh. This prevents the entire walking assist device 120 from shifting with respect to the leg of the trainee 900.

System Configuration Example of Walking Training Device

Figure 4:
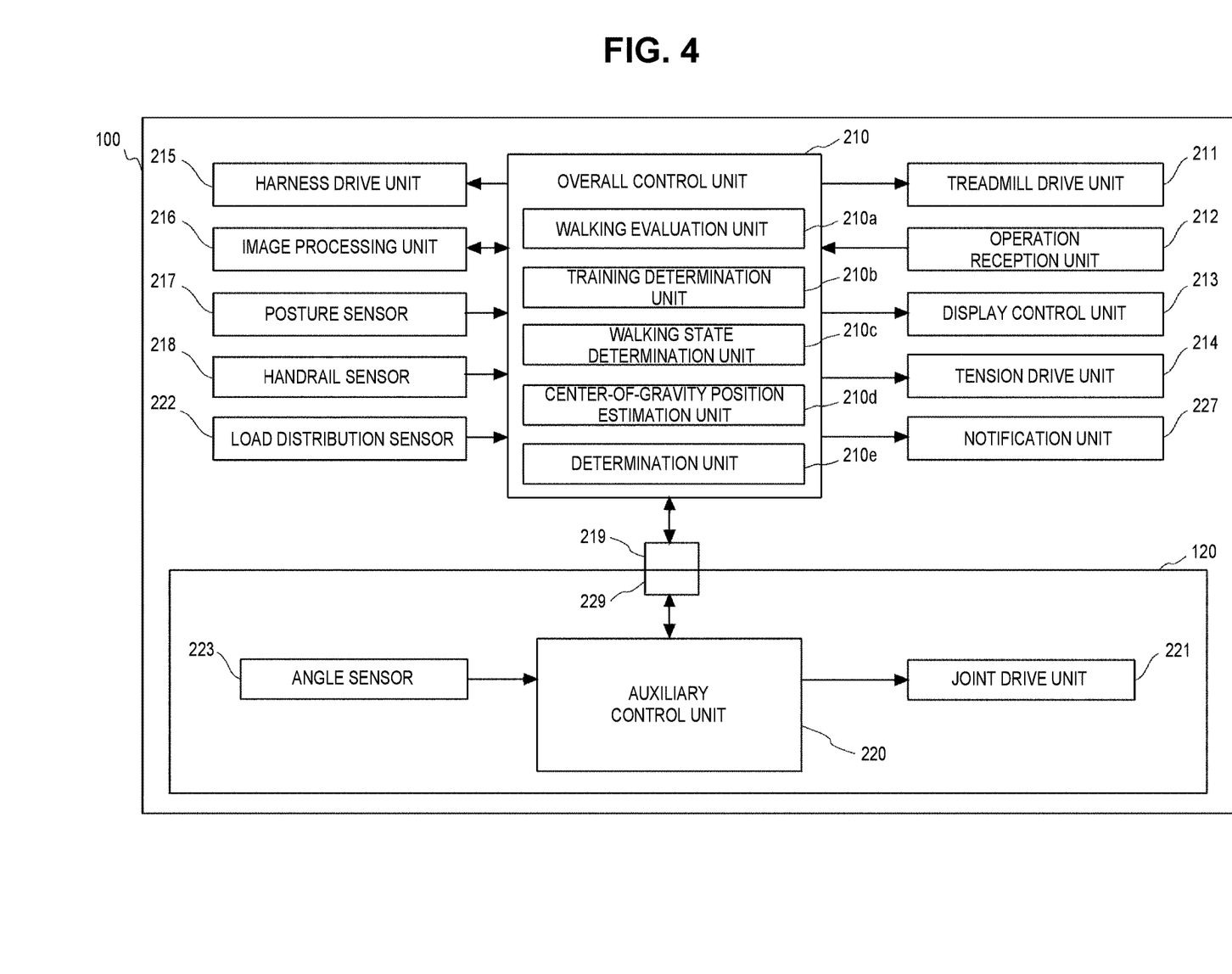
FIG. 4 is a block diagram illustrating a system configuration example of the walking training device illustrated in FIG. 1.

Subsequently, a system configuration example of the walking training device 100 will be described with reference to FIG. 4. FIG. 4 is a block diagram illustrating the system configuration example of the walking training device 100.

As illustrated in FIG. 4, the system configuration of the walking training device 100 includes the overall control unit 210, a treadmill drive unit 211, an operation reception unit 212, a display control unit 213, a harness drive unit 215, an image processing unit 216, the posture sensor 217 which is an example of the posture detection unit 226, the handrail sensor 218, the load distribution sensor 222 which is an example of the center-of-gravity position detection unit 225, a communication connection interface (IF) 219, and the walking assist device 120.

The overall control unit 210 may be, for example, a micro processing unit (MPU), and controls the entire device by executing a control program read from a system memory.

The treadmill drive unit 211 includes a motor used for rotating the belt 1311 of the treadmill 131 and a drive circuit thereof. The overall control unit 210 executes rotation control of the belt 1311 by sending a drive signal to the treadmill drive unit 211. The overall control unit 210 adjusts the rotation speed of the belt 1311 according to, for example, the walking speed set by the training staff member 901. Alternatively, the overall control unit 210 adjusts the rotation speed of the belt 1311 according to the walking state of the trainee 900 determined from the detection result of the load distribution sensor 222.

The operation reception unit 212 receives an input operation by the training staff member 901 via an operation button provided on the device, the touch panel superimposed on the management monitor 139, an attached remote controller, or the like. The operation signal received by the operation reception unit 212 is transmitted to the overall control unit 210. The overall control unit 210 can give an instruction to switch the power on and off or give an instruction to start training based on the operation signal received by the operation reception unit 212. In addition, it is possible to enter numerical values related to settings and select the menu items. The operation reception unit 212 is not limited to accepting the input operation of the training staff member 901, and certainly can also accept the input operation of the trainee 900.

The display control unit 213 receives the display signal from the overall control unit 210, generates a display image, and displays it on the training monitor 138 or the management monitor 139. The display control unit 213 generates an image showing the progress of training and a real-time image captured by the camera 140 according to the display signal.

A tension drive unit 214 includes a motor used for pulling the front wire 134 and a drive circuit thereof that are provided in the front tension unit 135, and a motor used for pulling the rear wire 136 and a drive circuit thereof that are provided in the rear tension unit 137. The overall control unit 210 controls the winding of the front wire 134 and the winding of the rear wire 136 by sending a drive signal to the tension drive unit 214. Further, the overall control unit 210 controls the tensile force of each wire by controlling the drive torque of the motor, not limited to the winding operation. Further, the overall control unit 210 identifies, for example, a timing at which the affected leg switches from the standing state to the swinging state from the detection result of the load distribution sensor 222 and assists the swinging motion of the affected leg by increasing or decreasing the tensile force of each wire in synchronization with the timing.

The harness drive unit 215 includes a motor used for pulling the harness wire 111 and a drive circuit thereof that are provided in the harness tension unit 112. The overall control unit 210 controls the winding of the harness wire 111 and the tensile force of the harness wire 111 by sending a drive signal to the harness drive unit 215. The overall control unit 210 winds a certain amount of the harness wire 111 to prevent the trainee 900 from falling, for example, when it is predicted that the trainee 900 will fall.

The image processing unit 216 is connected to the camera 140 and can receive an image signal from the camera 140. The image processing unit 216 receives the image signal from the camera 140 according to the instruction from the overall control unit 210, and performs image processing on the received image signal to generate image data. Further, the image processing unit 216 can also perform the image processing on the image signal received from the camera 140 according to the instruction from the overall control unit 210 to perform a specific image analysis. For example, the image processing unit 216 detects a position (a standing position) of the foot of the affected leg in contact with the treadmill 131 by image analysis. Specifically, for example, the standing position is calculated by extracting an image region near a tip of the foot flat frame 124 and analyzing an identification marker drawn on the belt 1311 overlapping the tip.

The posture sensor 217, which is an example of the posture detection unit 226, detects the inclination angle of the abdomen of the trainee 900 with respect to the gravity direction as described above, and transmits a detection signal to the overall control unit 210. The overall control unit 210 calculates the posture of the trainee 900, specifically, an inclination angle of the trunk, using the detection signal from the posture sensor 217. The overall control unit 210 and the posture sensor 217 may be connected by wire or by near-field wireless communication.

The posture detection unit 226 is not limited to the posture sensor 217, and may be composed of, for example, a camera (a second image capturing unit; for example, the camera 140) that captures an image of the whole body of the trainee 900 on the belt 1311 of the treadmill 131, and a posture information extraction unit that extracts information on the posture of the trainee 900 from the images captured by the camera.

Alternatively, the posture detection unit 226 may be composed of an infrared sensor that detects the trainee 900 on the belt 1311 of the treadmill 131, and a posture information extraction unit that extracts information on the posture of the trainee 900 from the detection result by the infrared sensor.

The handrail sensor 218 detects a load applied to the handrail 130a. In other words, the load that the trainee 900 cannot support with his or her legs out of his or her own weight is applied to the handrail 130a. The handrail sensor 218 detects the load and sends a detection signal to the overall control unit 210.

The load distribution sensor 222 detects the magnitude and distribution of the surface pressure (the load) received from the sole of the trainee 900 as described above, and transmits the detection signal to the overall control unit 210. The overall control unit 210 receives the detection signal and analyzes it to determine the walking state and estimate the switching. Here, the load distribution sensor 222 can also detect a center-of-gravity position (an actual center-of-gravity position) CP of the trainee 900 from the load received from the sole of the trainee 900 as the center-of-gravity position detection unit 225.

The center-of-gravity position detection unit 225 is not limited to the load distribution sensor 222, and may be composed of, for example, a pair of load sensors respectively attached to the soles of the right and left legs of the trainee 900, and a camera (a first image capturing unit; for example, the camera 140) that captures the feet of the trainee 900 on the belt 1311 of the treadmill 131. In this case, the center-of-gravity position CP of the trainee 900 is detected based on the load detected by the pair of load sensors and the positions of the right leg and the left leg of the trainee 900 identified from the captured image of the camera.

The overall control unit 210 also serves as a function execution unit that executes control or various calculations associated with control. The overall control unit 210 includes, for example, a walking evaluation unit 210a, a training determination unit 210b, a walking state determination unit 210c, a center-of-gravity position estimation unit 210d, and a determination unit 210e. The center-of-gravity position estimation unit 210d and the determination unit 210e will be described below.

The walking evaluation unit 210a evaluates whether the walking motion of the trainee 900 is abnormal walking by using the data acquired from various sensors. The training determination unit 210b determines, for example, the training results of a series of walking training sessions based on the cumulative number of instances of abnormal walking evaluated by the walking evaluation unit 210a.

The method and criteria of determining the training results may be arbitrarily set. For example, the training results may be determined by comparing the amount of movement of the paralyzed body with the standard amount for each walking phase. The walking phase refers to phases of one walking cycle (one walk cycle) for the affected leg (or a healthy leg) which are classified into a standing phase in which the leg is in the standing state, a transition phase from the standing phase to the swinging phase in which the leg is in the swinging state, the swinging phase, a transition phase from the swinging phase to the standing phase, and the like. Which walking phase the leg is in can be classified (determined) from, for example, the detection result by the load distribution sensor 222. As described above, the walking cycle consisting of the standing phase, the transition phase, the swinging phase, and the transition phase can be treated as one cycle, but it does not matter which phase is defined as the start phase. In addition, the walking cycle consisting of, for example, a both-leg supporting state, a single-leg (the affected leg) supporting state, a both-leg supporting state, and a single-leg (the healthy leg) supporting state can be treated as one cycle. In this case as well, it does not matter which state is defined as the start state.

In addition, the walking cycle focusing on the right leg or the left leg (the healthy leg or the affected leg) can be further subdivided. For example, the standing phase can be divided into and expressed as initial ground contact and four phases, and the swinging phase can be divided into and expressed as three phases. The initial ground contact refers to the moment when the observation foot touches the floor, and the four phases of the standing phase refer to a load response phase, a middle standing phase, a final standing phase, and a pre-swinging phase. The load response phase is a period from the initial ground contact to the moment when the foot on an opposite side leaves the floor (contralateral ground takeoff). The middle standing phase is a period from the contralateral ground takeoff to the moment when the heel of the observation foot moves away (heel takeoff). The final standing phase is a period from the heel takeoff to the initial ground contact on the opposite side. The pre-swinging phase is a period from the initial ground contact on the opposite side to the time when the observation foot leaves the floor (takeoff). The three phases of the swinging phase refer to an initial swinging phase, a middle swinging phase, and a final swinging phase. The initial swinging phase is a period from the end of a previous swinging phase (the ground takeoff described above) to the time when both feet cross (foot crossing). The middle swinging phase is a period from the foot crossing to the time when the cervical spine becomes vertical (a vertical state of cervical spine). The final swing phase is a period from the vertical state of the cervical spine to the next initial ground contact.

The walking state determination unit 210c determines the walking state of the trainee 900 based on the load distribution of each leg detected by the load distribution sensor 222. For example, when the load that is received from a first leg of the trainee 900 and detected by the load distribution sensor 222 changes from a state where the load is lower than a first threshold value to a state where the load is equal to or higher than the first threshold value, the walking state determination unit 210c determines that the state of the first leg has changed from the swinging state to the standing state. In addition, when the state changes from a state where the load is equal to or higher than a second threshold value (first threshold value > second threshold value) to a state where the load is lower than the second threshold value, the walking state determination unit 210c determines that the state of the first leg has changed from the standing state to the swinging state. Similarly, when the load that is received from a second leg of the trainee 900 and detected by the load distribution sensor 222 changes from a state where the load is lower than the first threshold value to a state where the load is equal to or higher than the first threshold value, the walking state determination unit 210c determines that the state of the second leg has changed from the swinging state to the standing state. In addition, when the state changes from a state where the load is equal to or higher than the second threshold value (first threshold value > second threshold value) to a state where the load is lower than the second threshold value, the walking state determination unit 210c determines that the state of the second leg has changed from the standing state to the swinging state. The walking state determination unit 210c determines not only the walking state of the healthy leg but also the walking state of the affected leg equipped with the walking assist device 120. In that case, the walking state determination unit 210c determines the walking state in consideration of the load of the walking assist device 120. For example, the flexion and extension control of the affected leg is performed by the walking assist device 120 based on the determination result of the walking state determination unit 210c.

The communication connection IF 219 is an interface connected to the overall control unit 210, and is an interface used for giving a command to the walking assist device 120 mounted on the affected leg of the trainee 900 and receiving sensor information.

The walking assist device 120 can include a communication connection IF 229 that is connected to the communication connection IF 219 in a wired or wireless manner. The communication connection IF 229 is connected to the auxiliary control unit 220 of the walking assist device 120. The communication connection IFs 219, 229 are communication interfaces, such as a wired LAN or a wireless LAN, according to a communication standard.

Further, the walking assist device 120 can include the auxiliary control unit 220, a joint drive unit 221, and the angle sensor 223. The auxiliary control unit 220 may be, for example, an MPU, and controls the walking assist device 120 by executing a control program given by the overall control unit 210. Further, the auxiliary control unit 220 notifies the overall control unit 210 of the state of the walking assist device 120 via the communication connection IFs 219, 229. Further, the auxiliary control unit 220 receives a command from the overall control unit 210 and executes control such as starting and stopping the walking assist device 120.

The joint drive unit 221 includes a motor of the control unit 121 and a drive circuit thereof. The auxiliary control unit 220 applies force to the upper thigh frame 122 and the lower thigh frame 123 to open or close relatively around the hinge axis Ha by sending a drive signal to the joint drive unit 221. Such movements assist the knee extension and flexion movements and prevent the knee from becoming fractured.

As described above, the angle sensor 223 detects the angle formed by the upper thigh frame 122 and the lower thigh frame 123 around the hinge axis Ha, and transmits the detection signal to the auxiliary control unit 220. The auxiliary control unit 220 receives the detection signal and calculates the opening angle of the knee joint.

In the case where the trainee 900 is performing walking training with the support of the training staff member 901, when the training staff member 901 excessively supports the trainee 900, the trainee 900 cannot perform effective walking training when no further measures are taken.

Therefore, the walking training device 100 according to the present embodiment has a function of sending a notification to the training staff member 901 when the support of the trainee 900 by the training staff member 901, who is an assistant, is excessive. As a result, the training staff member 901 who has received the notification can offer the trainee 900 less support, such that the trainee 900 can perform effective walking training.

Specifically, first, the center-of-gravity position estimation unit 210d estimates a center-of-gravity position CPx of the trainee 900 from the posture of the trainee 900 detected by the posture detection unit 226, such as the posture sensor 217. For example, the center-of-gravity position estimation unit 210d estimates the center-of-gravity position CPx of the trainee 900 by applying, for example, the weight and center of gravity of each part stored in a database to the posture of the trainee 900 detected by the posture detection unit 226, such as the posture sensor 217. In this case, the center-of-gravity position detection unit 225, such as the load distribution sensor 222, detects the actual center-of-gravity position CP of the trainee 900.

Then, the determination unit 210e determines whether a difference (a deviation) between the actual center-of-gravity position CP detected by the center-of-gravity position detection unit 225 and the center-of-gravity position CPx estimated from the posture of the trainee 900 by the center-of-gravity position estimation unit 210d exceeds a predetermined value T1. When the determination unit 210e determines that the difference between the actual center-of-gravity position CP and the center-of-gravity position CPx estimated from the posture of the trainee 900 exceeds the predetermined value T1, the notification unit 227 notifies the training staff member 901 that the support for the trainee 900 by the training staff member 901 is excessive.

Figure 5:
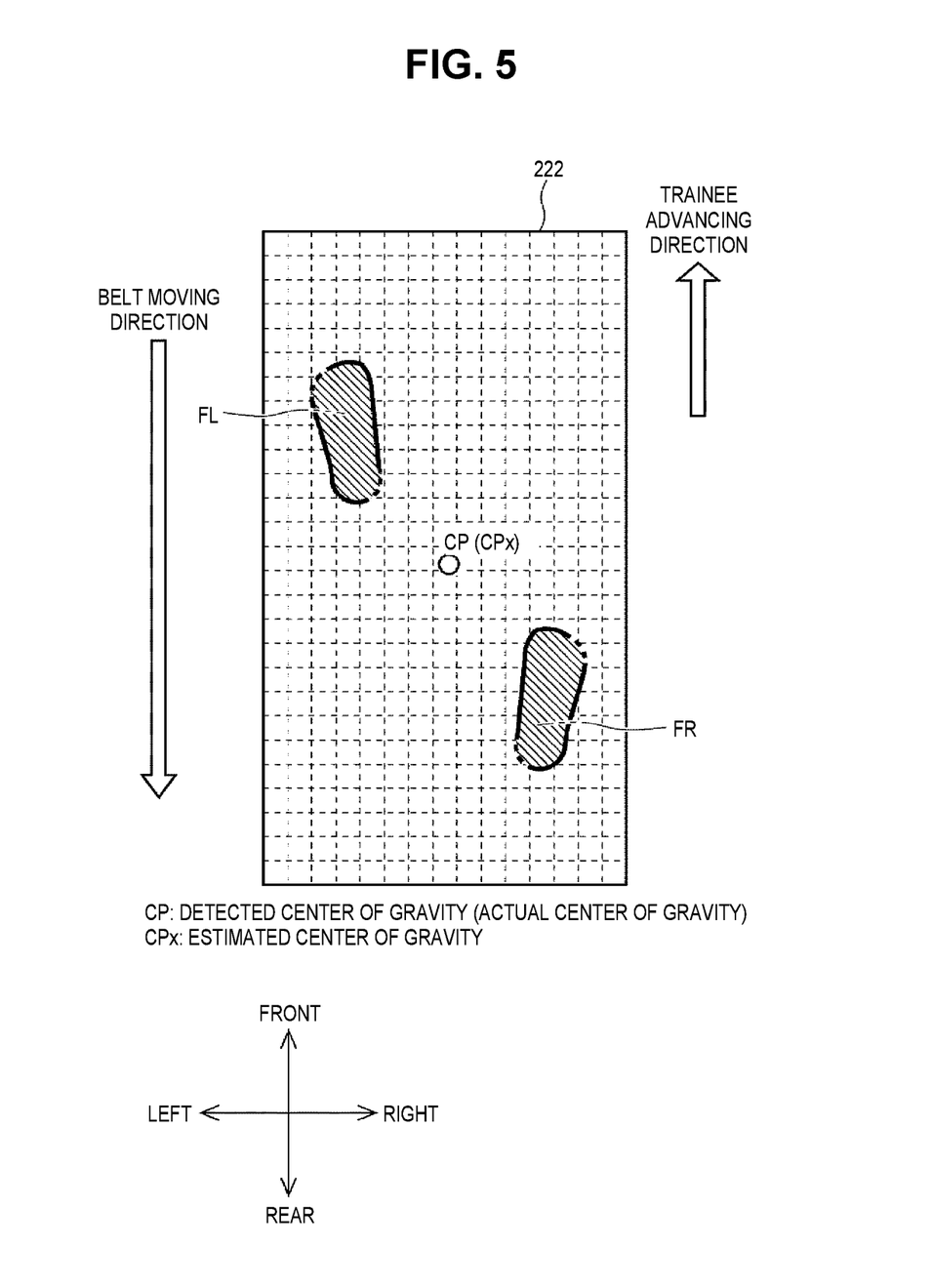
FIG. 5 is a diagram used for illustrating an operation of the walking training device illustrated in FIG. 1.
Figure 6:
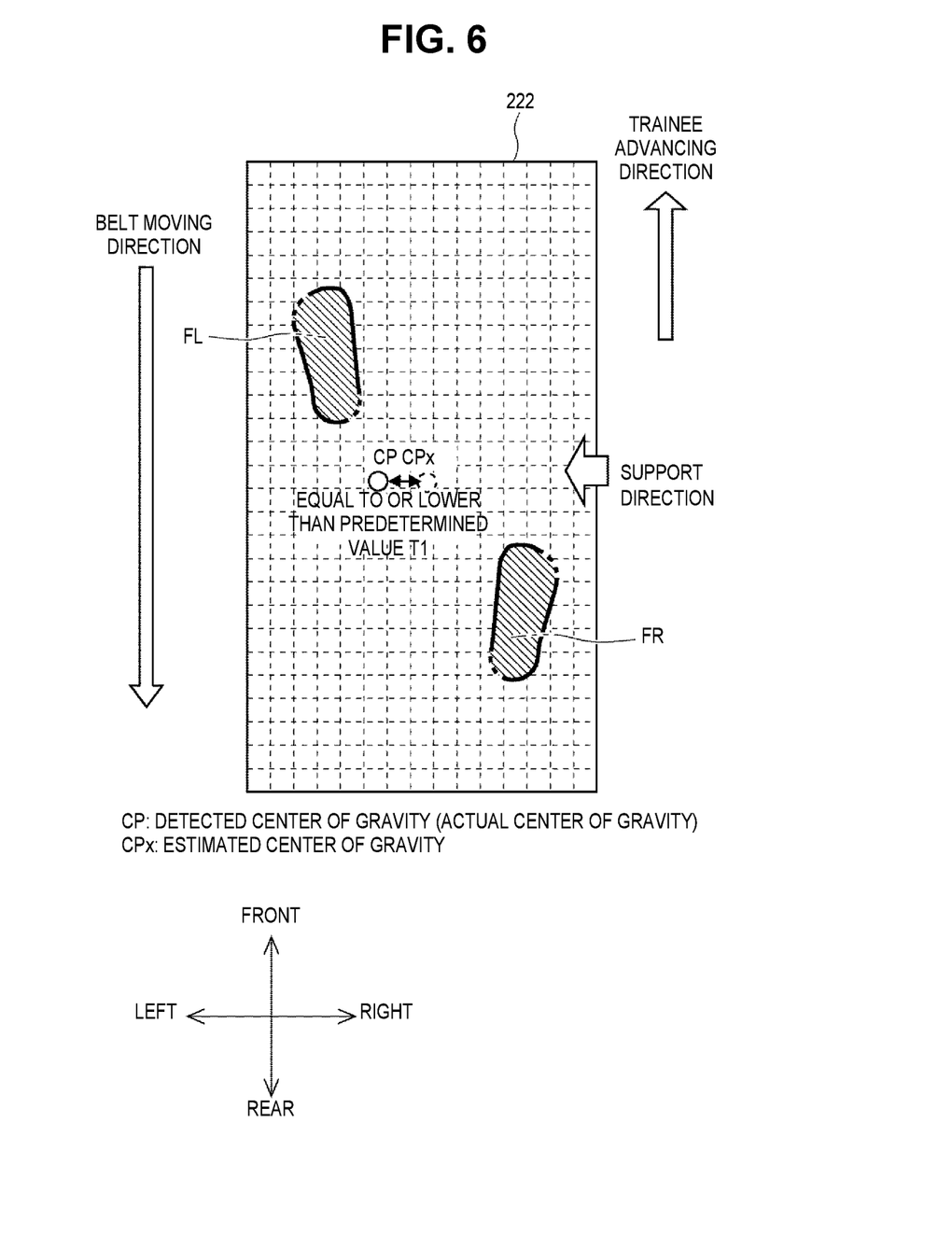
FIG. 6 is a diagram used for illustrating the operation of the walking training device illustrated in FIG. 1.
Figure 7:
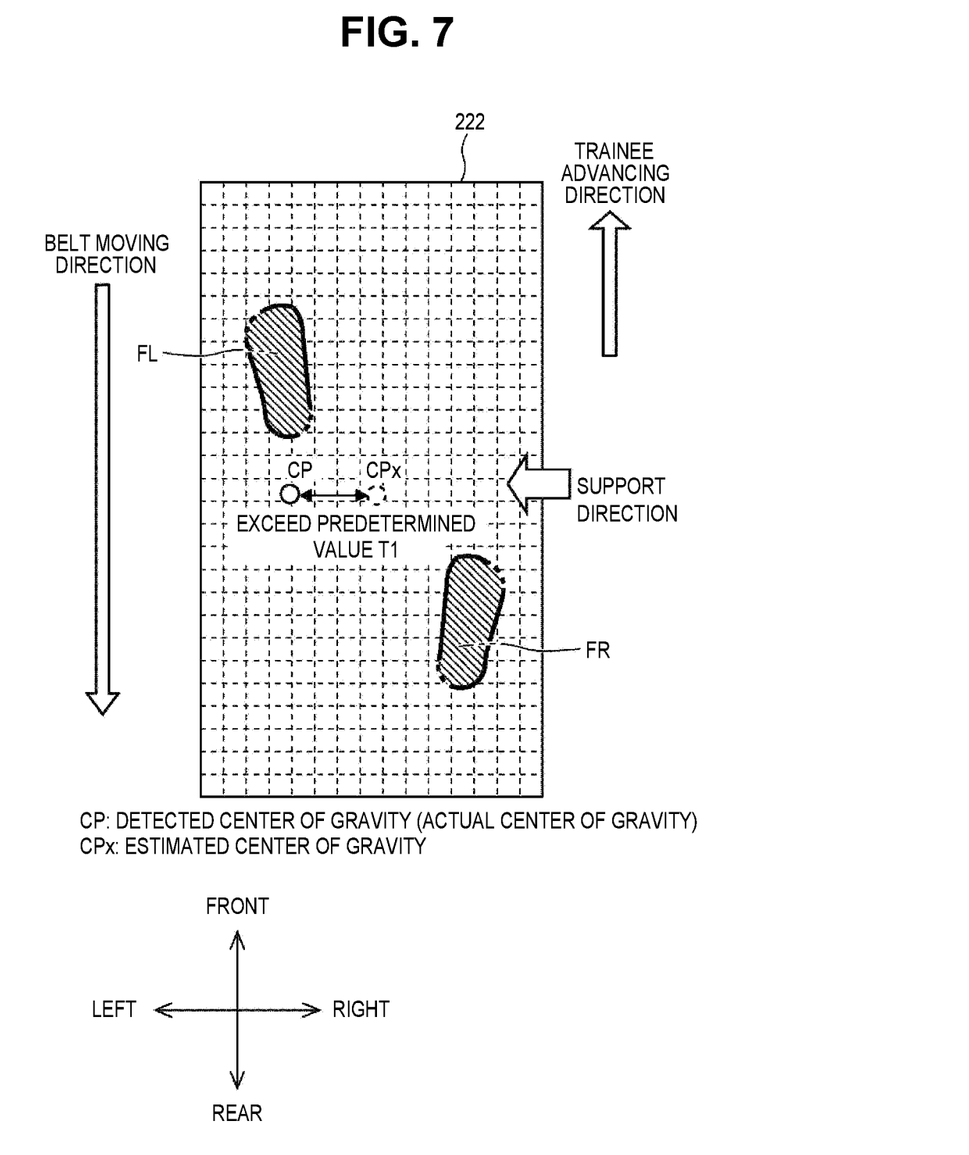
FIG. 7 is a diagram used for illustrating the operation of the walking training device illustrated in FIG. 1.

FIGS. 5 to 7 are diagrams used for illustrating the operation of the walking training device 100. First, in the example of FIG. 5, since the training staff member 901 does not support the trainee 900, the difference between the actual center-of-gravity position CP and the center-of-gravity position CPx estimated from the posture of the trainee 900 is substantially zero. In this case, since the difference between the actual center-of-gravity position CP and the center-of-gravity position CPx estimated from the posture of the trainee 900 is equal to or lower than the predetermined value T1, the determination unit 210e determines that the support for the trainee 900 by the training staff member 901 is not excessive. Therefore, the notification unit 227 does not send a notification.

When there is a deviation (an error value) between the center-of-gravity position CP and the center-of-gravity position CPx in a state where the training staff member 901 is not supporting the trainee 900, the determination unit 210e may subtract the error value and determine whether the deviation between the center-of-gravity position CP and the center-of-gravity position CPx exceeds the predetermined value T1. Alternatively, the predetermined value T1 may be set to a value that offsets the deviation (the error value) between the center-of-gravity position CP and the center-of-gravity position CPx in the state where the training staff member 901 does not support the trainee 900.

Next, in the example of FIG. 6, the training staff member 901 supports the trainee 900 from the right side to the left. However, the support for the trainee 900 by the training staff member 901 is not excessive, and thus the actual center-of-gravity position CP has a small deviation to the left. In this case, since the difference between the actual center-of-gravity position CP and the center-of-gravity position CPx estimated from the posture of the trainee 900 is equal to or lower than the predetermined value T1, the determination unit 210e determines that the support for the trainee 900 by the training staff member 901 is not excessive. Therefore, the notification unit 227 does not send a notification.

Next, in the example of FIG. 7, the training staff member 901 supports the trainee 900 from the right side to the left. However, the support for the trainee 900 by the training staff member 901 is excessive, and thus the actual center-of-gravity position CP has a large deviation to the left. In this case, since the difference between the actual center-of-gravity position CP and the center-of-gravity position CPx estimated from the posture of the trainee 900 exceeds the predetermined value T1, the determination unit 210e determines that the support for the trainee 900 by the training staff member 901 is excessive. Therefore, the notification unit 227 notifies the training staff member 901 that the support for the trainee 900 by the training staff member 901 is excessive. As a result, the training staff member 901 who has received the notification can, for example, offer the trainee 900 less support, and thus the trainee 900 can perform effective walking training.

As described above, the walking training device 100 according to the present embodiment has a function of sending a notification to the training staff member 901 when the support for the trainee 900 by the training staff member 901 is excessive. As a result, the training staff member 901 who has received the notification can, for example, offer the trainee 900 less support, such that the trainee 900 can perform effective walking training.

As described above, the predetermined value T1 may be set to a value that offsets the deviation (the error) between the center-of-gravity position CP and the center-of-gravity position CPx in the state where the training staff member 901 does not support the trainee 900. Further, the predetermined value T1 may be adjusted in real time according to at least one of the walking speed of the trainee 900 and the motion speed of a predetermined part (an arm or the like) of the trainee 900. For example, since the error of the center-of-gravity position CPx estimated from the posture of the trainee 900 tends to increase as the walking speed of the trainee 900 increases, the predetermined value T1 may be set to a high value. Also, since the error of the center-of-gravity position CPx tends to become smaller as the walking speed of the trainee 900 becomes slower, the predetermined value T1 may be set to a low value.

Further, in the present embodiment, the case where the notification unit 227 notifies the trainee 900 when the support for the trainee 900 by the training staff member 901 is excessive is described as an example, but the present disclosure is not limited thereto. For example, when a predetermined abnormal movement of the trainee 900 is detected, such as when the trainee 900 is clearly about to fall, it is useless to determine whether the support for the trainee 900 by the training staff member 901 is excessive, and thus the notification unit 227 does not have to send a notification.

Further, in the present embodiment, the case where the trainee 900 is a hemiplegic patient suffering from paralysis in one leg is described as an example, but the present disclosure is not limited thereto. The trainee 900 may be, for example, a patient suffering from paralysis of both legs. In that case, the trainee 900 attaches the walking assist devices 120 to respective legs to perform the training. Alternatively, the trainee 900 does not have to be equipped with the walking assist device 120 on any of the legs.

Further, the present disclosure can be implemented by causing a central processing unit (CPU) to execute a computer program in part or all of the processing in the walking training device 100.

The program includes a set of instructions (or software codes) for causing a computer to perform one or more of the functions described in the embodiments when loaded onto the computer. The program may be stored in a non-transitory computer-readable medium or a tangible storage medium. As an example but not a limitation, a computer-readable medium or a tangible storage medium includes a random-access memory (RAM), a read-only memory (ROM), a flash memory, a solid-state drive (SSD) or other memory technology, a CD-ROM, a digital versatile disc (DVD), a Blu-ray® disc or other optical disc storages, a magnetic cassette, a magnetic tape, and a magnetic disk storage or other magnetic storage devices. The program may be transmitted on a transitory computer-readable medium or a communication medium. As an example but not a limitation, the transitory computer-readable medium or the communication medium includes electrical, optical, acoustic, or other forms of propagating signals.

What is claimed is:
1. A walking training system comprising:
   a treadmill;
   a load distribution sensor configured to detect a center-of-gravity position of a trainee, the load distribution sensor being installed under a belt of the treadmill such that the load distribution sensor is not interlocked with the belt and is configured to detect a distribution of a load applied by a sole of the trainee on the belt of the treadmill;

a posture sensor configured to detect a posture of the trainee, the posture sensor being a combination of a gyro sensor and an acceleration sensor disposed on an orthotic device configured to be attached to an abdomen of the trainee; and a processor configured to
estimate the center-of-gravity position of the trainee from the detected posture of the trainee;
determine whether a difference between the detected center-of-gravity position and the estimated center-of-gravity position exceeds a predetermined value; and
send a notification notifying that the difference exceeds the predetermined value when the processor determines that the difference exceeds the predetermined value, wherein the predetermined value is determined according to at least one of a walking speed of the trainee and a motion speed of a predetermined part of the trainee.

2. The walking training system according to claim 1, wherein
the predetermined value is determined according to the walking speed of the trainee, and
the predetermined value is set to a larger value as the walking speed of the trainee becomes faster, and is set to a smaller value as the walking speed of the trainee becomes slower.

3. The walking training system according to claim 1, wherein the predetermined value is determined such that the difference between the detected center-of-gravity position and the estimated center-of-gravity position is offset when an assistant does not support the trainee.

4. The walking training system according to claim 1, wherein, the processor is configured not to, when a predetermined abnormal movement is detected, send the notification even when the difference between the detected center-of-gravity position and the estimated center-of-gravity position exceeds the predetermined value.

* * * * *